United States Patent [19]
Hibino et al.

[11] Patent Number: 6,120,652
[45] Date of Patent: Sep. 19, 2000

[54] METHOD FOR PURIFYING CRUDE 1,1,1,3,3-PENTAFLUOROPROPANE

[75] Inventors: Yasuo Hibino; Ryouichi Tamai, both of Saitama, Japan

[73] Assignee: Central Glass Company, Ube, Japan

[21] Appl. No.: 09/038,146

[22] Filed: Mar. 10, 1998

[30] Foreign Application Priority Data

| Mar. 11, 1997 | [JP] | Japan | 9-056216 |
| Apr. 10, 1997 | [JP] | Japan | 9-092127 |
| Jan. 27, 1998 | [JP] | Japan | 10-013951 |

[51] Int. Cl.⁷ ............................ B01D 3/40; C07C 17/386
[52] U.S. Cl. .................. 203/51; 203/52; 203/57; 203/67; 203/68; 203/69; 203/70; 570/178
[58] Field of Search ................... 203/67, 69, 51, 203/68, 70, 52, 57; 570/177, 178, 166–169; 252/364

[56] References Cited

U.S. PATENT DOCUMENTS

| 5,087,329 | 2/1992 | Felix . | |
| 5,574,192 | 11/1996 | VanDerPuy et al. . | |
| 5,672,294 | 9/1997 | Lund et al. | 252/67 |
| 5,710,352 | 1/1998 | Tung | 270/166 |
| 5,788,886 | 8/1998 | Minor et al. | 252/364 |
| 5,811,603 | 9/1998 | Elsheikh | 570/166 |
| 6,039,845 | 3/2000 | Bertocchio et al. | 203/57 |

FOREIGN PATENT DOCUMENTS

| 0729932 | 4/1996 | European Pat. Off. . |
| 7-133240 | 5/1995 | Japan . |
| 9-12487 | 1/1997 | Japan . |
| 97/08117 | 3/1997 | WIPO . |
| 9800379 | 1/1998 | WIPO . |

*Primary Examiner*—Virgina Manoharan
*Attorney, Agent, or Firm*—Evenson, McKeown, Edwards & Lenahan, P.L.L.C.

[57] ABSTRACT

The invention relates to a method for purifying a crude 1,1,1,3,3-pentafluoropropane (HFC-245fa) containing HFC-245fa and 1-chloro-3,3,3-trifluoro-trans-1-propene (HCFC-1233zd(t)), by distillation. This method is characterized in that the distillation is conducted in the presence of a solvent having a boiling point which is higher than that of HCFC-1233zd(t), thereby to substantially remove HCFC-1233zd(t) from the crude HFC-245fa. This solvent may be selected from carbon chlorides, chlorohydrocarbons, fluorochlorohydrocarbons, saturated hydrocarbons, and mixtures thereof. With the use of this solvent, it becomes possible to substantially easily separate HFC-245fa from HCFC-1233zd(t).

17 Claims, No Drawings

METHOD FOR PURIFYING CRUDE 1,1,1,3,3-PENTAFLUOROPROPANE

BACKGROUND OF THE INVENTION

The present invention relates to a method for purifying 1,1,1,3,3-pentafluoropropane (hereinafter referred to as "HFC-245fa") which is useful as a refrigerant, a blowing agent for preparing rigid urethane foam, and the like, particularly to a method for purifying a crude HFC-245fa containing 1-chloro-3,3,3-trifluoro-trans-1-propene and the like, which are to be removed therefrom.

Today, 1,1-dichloro-1-fluoroethane is used as a blowing agent for preparing rigid urethane foam, and the like. This compound has a capability to destroy the ozone layer, even though its capability is low. Therefore, it is considered as a transient alternative substance and thus is designated as an object which will be limited in use in the future. In view of this, much attention is attracted to HFC-245fa as being an alternative to 1,1-dichloro-1-fluoroethane, since HFC-245fa does not have a capability to destroy the ozone layer.

There is disclosed in U.S. Pat. No. 5,574,192 a method for producing HFC-245fa by fluorinating 1,1,1,3,3-pentachloropropane with hydrogen fluoride in the liquid phase in the presence of a fluorination catalyst of antimony pentachloride. In case that this fluorination is conducted continuously, an intermediate of this fluorination, 1-chloro-3,3,3-trifluoro-1-propene (hereinafter referred to as HCFC-1233zd), will inevitably be distilled off together with HFC-245fa, since these compounds are close in boiling point. This intermediate, HCFC-1233zd, has cis-trans isomers (HCFC-1233zd(c) and HCFC-1233zd(t)). When 1,1,1,3,3-pentachloropropane or HCFC-1233zd is reacted in the gas phase with hydrogen fluoride in the presence of a chromium catalyst and the like, the reaction product may contain a considerable amount of HCFC-1233zd.

In general, distillation is used for separating a liquid or gaseous liquefiable mixture. It is, however, very difficult to separate components of this mixture, if they are close in boiling point. For example, the boiling points of HFC-245fa and HCFC-1233zd(t) are very close, 15.3° C. for HFC-245fa and 21.0° C. for HCFC-1233zd(t). In a normal distillation of a mixture containing HFC-245fa and HCFC-1233zd(t), HCFC-1233zd(t) is distilled off, prior to HFC-245fa. Thus, the relative volatility of these components is assumed to be close to 1. It is known to use extractive distillation in order to effectively separate a mixture containing components having a relative volatility close to 1. There is disclosed in U.S. Pat. No. 5,087,329 the use of 1,2-dichlorotetrafluoroethane as an extractive agent, in an extractive distillation for separating pentafluoroethane from chloropentafluoroethane. Furthermore, there is disclosed in Japanese Patent Unexamined Publication JP-A-7-133240 the use of an extractive agent selected from paraffines (alkanes), alcohols, ethers and ketones, which have standard boiling points under atmospheric pressure within a range of from −10 to 100° C., in an extractive distillation for separating pentafluoroethane from chloropentafluoroethane. Still furthermore, there is disclosed in JP-A-9-12487 the use of an extractive agent selected from carbon chlorides and chlorohydrocarbons, having 1–2 carbon atoms in the molecule, in an extractive distillation for separating pentafluoroethane from 1,1,1-trifluoroethane.

SUMMARY OF THE INVENTION

It is an object of the present invention to provide a method for substantially easily purifying a crude HFC-245fa containing HCFC-1233zd(t) which is to be removed therefrom.

According to the present invention, there is provided a method for purifying a crude 1,1,1,3,3-pentafluoropropane (i.e., HFC-245fa) comprising HFC-245fa and 1-chloro-3,3,3-trifluoro-trans-1-propene (i.e., HCFC-1233zd(t)), by distillation. This method is characterized in that the distillation is conducted in the presence of a solvent having a boiling point which is higher than that of HCFC-1233zd(t), thereby to substantially remove HCFC-1233zd(t) from the crude HFC-245fa. This solvent may be selected from the group consisting of carbon chlorides, chlorohydrocarbons, fluorochlorohydrocarbons, saturated hydrocarbons, and mixtures thereof. With the use of this solvent, it becomes possible to substantially easily separate HFC-245fa from HCFC-1233zd(t) contained in the crude HFC-245fa.

DESCRIPTION OF THE PREFERRED EMBODIMENTS

A method for purifying a crude HFC-245fa containing HFC-245fa and HCFC-1233zd(t) which is to be removed therefrom, by distillation will be described in detail in accordance with the present invention, as follows.

In general, the crude HFC-245fa varies in composition, depending on the reaction conditions for preparing the same. In fact, the position of chemical equilibrium is influenced by the reaction conditions such as the reaction temperature, pressure, and the hydrogen chloride concentration of the reaction system, and thus the crude HFC-245fa has a certain particular composition. In general, the reaction conditions are adjusted in a manner to maximize the production efficiency and to minimize the production cost. In the invention, the crude HFC-245fa is not particularly limited in composition. In the crude HFC-245fa, the molar ratio of HCFC-1233zd(t) to HFC-245fa may be from 0.01:1 to 1:1. If this ratio exceeds 1, it does not cause any technical problems. However, the amount of HCFC-1233zd(t) to be recycled may become too much. This is not preferable from the economical viewpoint.

The method for producing the crude HFC-245fa which contains HFC-245fa and HCFC-1233zd (i.e., a mixture of cis-trans isomers) and is to be purified in accordance with the present invention is not particularly limited. For example, this crude HFC-245fa may be produced by fluorinating a propane represented by the formula $CF_yCl_{3-y}CH_2CHF_WCl_{2-W}$ where W is 0 or 1 and Y is an integer of from 0 to 3, with hydrogen fluoride, in the presence of a catalyst, in the liquid phase. In particular, the crude HFC-245fa may be produced by fluorinating 1,1,1,3,3-pentachloropropane with hydrogen fluoride, in the liquid phase, in the presence of an antimony compound as catalyst. Furthermore, the crude HFC-245fa may be produced by fluorinating 1,1,1,3,3-pentachloropropane or HCFC-1233zd with hydrogen fluoride, in the gas phase, in the presence of a chromium catalyst.

According to the above-mentioned methods for producing the crude HFC-245fa, the reaction products obtained from the reaction system are the following first, second or third compound and the unreacted hydrogen fluoride, as well as hydrogen chloride and HFC-245fa. This first compound is represented by the formula $CF_YCl_{3-Y}CH_2CHF_WCl_{2-W}$ where Y is an integer of from 0 to 3, W is an integer of from 0 to 2, and it is impossible that Y is 3 and at the same time W is 2. In fact, when Y is 3 and at the same time W is 2, the first compound becomes HFC-245fa. The second compound is represented by the formula $CHF_MCl_{2-M}CH=CF_NCl_{2-N}$ where M is an integer of from 0 to 2, N is an integer of from 0 to 2. The third compound is represented by the formula $CHF_PCl_{1-P}CHCF_QCl_{3-Q}$ where P is 0 or 1, and Q is an integer of from 0 to 3. In general, the above-mentioned reaction products include HCFC-1233zd, and this HCFC-1233zd is made up of HCFC-1233zd(t) and HCFC-1233zd (c). In general, the molar ratio of this HCFC-1233zd(t) to this HCFC-1233zd(c) is from 5:1 to 10:1. Irrespective of this molar ratio, the method of the present invention can be used for purifying the crude HFC-245fa. It is, however, preferable to remove acid components (i.e., hydrogen chloride and hydrogen fluoride), for example, by washing the crude HFC-245fa with water or a basic solution or by a cooling condensation method, prior to the distillation of the present invention. The crude HFC-245fa used in the invention may be a mixture of the above-mentioned reaction products. Alternatively, this mixture may preliminarily be purified, for example, by distillation, to obtain a purified product which is substantially made up of HFC-245fa and HCFC-1233zd(t) and optionally HCFC-1233zd(c). This purified product may be used as the crude HFC-245fa of the invention.

The above-mentioned solvent used in the invention serves as an extracting reagent (extractive agent) in the distillation (i.e., extractive distillation). According to the invention, there is a first preferability that it is used as this solvent a substance which is capable of altering the volatility of HCFC-1233zd(t) relative to HFC-245fa and has a boiling point that is sufficiently higher than that of HCFC-1233zd(t), so that the solvent can easily be separated from HCFC-1233zd(t).

According to a first preferable embodiment of the invention, in addition to the above-mentioned first preferability, there are a second preferability that the solvent is selected from raw materials and intermediates of the production of the crude HFC-245fa, because the reaction is not influenced by the solvent contained in the reaction system when the residue of extractive distillation is recycled to the reactor, and a third preferability that the solvent is selected from nonflammable materials when it is used in an industrial scale. As the solvent according to the first embodiment of the invention, which satisfies the above-mentioned first, second and third preferabilities, it may be selected from the group consisting of carbon chlorides, chlorohydrocarbons, fluorochlorohydrocarbons, and mixtures thereof. As the solvent of the first preferable embodiment of the invention, which is selected from the above-mentioned raw materials and intermediates of the production of the crude HFC-245fa, it is preferably selected from the group consisting of first compounds represented by the formula $CF_YCl_{3-Y}CH_2CHF_WCl_{2-W}$ where Y is an integer of from 0 to 3, W is an integer of from 0 to 2, and it is impossible that Y is 3 and at the same time W is 2, second compounds represented by the formula $CHF_MCl_{2-M}CH=CF_NCl_{2-N}$ where M is an integer of from 0 to 2, N is an integer of from 0 to 2, and it is impossible that M is 2 and at the same time N is 2, third compounds represented by the formula $CHF_PCl_{1-P}CHCF_QCl_{3-Q}$ where P is 0 or 1, and Q is an integer of from 0 to 2, and mixtures thereof. Preferable examples of the above-mentioned chlorohydrocarbon used as the solvent are 1,1,1,3,3-pentachloropropane, 1,3,3,3-tetrachloropropene, and 1,1,3,3-tetrachloropropene. Preferable examples of the above-mentioned fluorochlorohydrocarbon used as the solvent are 1-fluoro-1,1,3,3-tetrachloropropane, 1,1-difluoro-1,3,3-trichloropropane, 1,3-difluoro-1,1,3-trichloropropane, 1,1,1-trifluoro-3,3-dichloropropane, 1,1,3-trifluoro-1,3-dichloropropane, and 1,1,1,3-tetrafluoro-3-chloropropane. Each of these preferable examples of chlorohydrocarbon and fluorochlorohydrocarbon is an intermediate, which is formed during a process for producing HFC-245fa from 1,1,1,3,3-pentachloropropane, 1,1,1,3-tetrachloropropene or 1,3,3,3-tetrachloropropene, or a compound derived from this intermediate. It is optional to use as the solvent of the invention a first mixture prepared by removing HFC-245fa, HCFC-1233zd(t) and compounds having boiling points lower than those of HFC-245fa and HCFC-1233zd(t), from the crude HFC-245fa formed by fluorination. Furthermore, it is optional to use as the solvent a second mixture prepared by removing some high-boiling-point components from the first mixture. According to the first embodiment of the invention, further preferable examples of the solvent are a chlorine-containing ethane having a chlorine atom number of from 3 to 5, a chlorine-containing ethylene having a chlorine atom number of from 3 to 4, a chlorine-containing methane having a chlorine atom number of from 2 to 3, and mixtures thereof. It is possible to cite as these further preferable examples of the solvent trichloroethylene, tetrachloroethylene, 1,1,2-trichloroethane, 1,1,2,2-tetrachloroethane, 1,1,1,2-tetrachloroethane, pentachloroethane, dichloromethane, and chloroform.

According to a second preferable embodiment of the invention, in addition to the above-mentioned first preferability, there is a fourth preferability that the solvent has a melting point which is not higher than about −10° C. so that the solvent does not solidify during the distillation nor make the solutes decrease in solubility. As the solvent of the second embodiment of the invention, which satisfies the above-mentioned first and fourth preferabilities, it may be selected from saturated hydrocarbons. Of these compounds, the solvent is preferably selected from saturated hydrocarbons having boiling points of from about 35 to about 200° C., and carbon atom numbers of from 5 to 10. Of such preferable compounds, the solvent is more preferably selected from an acyclic saturated hydrocarbon which is optionally formed with a branch and a cyclic saturated hydrocarbon which is optionally formed with a substituent group. Examples of this acyclic saturated hydrocarbon are n-pentane, n-hexane, 2-methylpentane, 3-methylpentane, 2,2-dimethylbutane, 2,3-dimethylbutane, n-heptane, 2-methylhexane, 3-methylhexane, 3-ethylpentane, 2,2-dimethylpentane, 2,3-dimethylpentane, 2,4-dimethylpentane, 3,3-dimethylpentane, 2,2,3-trimethylbutane, n-octane, n-nonane, and n-decane. Examples of the above-mentioned cyclic saturated hydrocarbon are cycloparaffines having carbon atom numbers of from 4 to 6 and alkyl-substituents, such as methylcyclobutane, ethylcyclobutane, 1,2-dimethylcyclobutane, isopropylcyclobutane, 1,2-diisopropylcyclobutane, cyclopentane, methylcyclopentane, ethylcyclopentane, propylcyclopentane, isopropylcyclopentane, butylcyclopentane, 1,2-dimethylcyclopentane, 1,3-dimethylcyclopentane, 1,1,3-trimethylcyclopentane, 1,2,4-trimethylcyclopentane, methylcyclohexane, ethylcyclohexane, n-propylcyclohexane, isopropylcyclohexane, n-butylcyclohexane, 1,1-dimethylcyclohexane, 1,2-dimethylcyclohexane, 1,2,3-trimethylcyclohexane, 1-ethyl-3-methylcyclohexane, and 1,2,3,4-tetramethylcyclohexane. These compounds are higher than HFC-245fa and HCFC-1233zd(t) in boiling point and may further have halogen-substituents (fluorine, chlorine, bromine and iodine).

The extractive distillation of the invention may be conducted by using a common distillation tower, preferably a packed tower or plate tower. In the extractive distillation, the extractive agent (i.e., solvent) is introduced into the extractive distillation tower above the stage of the fresh-feed of the crude HFC-245fa, in order to allow the solvent to be present throughout most of the distillation tower. Then, HFC-245fa is distilled off from the top of the tower, and a mixture of the solvent and HCFC-1233zd(t) is recovered from the tower. The operational conditions of the extractive distillation, such as the temperature at each stage of the tower, the position of the fresh-feed stage and the amount of the solvent to be introduced into the tower, are not particularly limited in the invention. These operation conditions may be changed, depending on the capability of the distillation tower, the ratio of HFC-245fa to HCFC-1233zd(t) in the fresh-feed, the type and the amount of the solvent, and the like, and can be determined by conducting a preliminary distillation test. It is optional to add the solvent to the fresh-feed, in order to stabilize the distillation operation. The extractive distillation of the invention may be conducted in a discontinuous or continuous manner. In an industrial scale, the extractive distillation in a continuous manner is preferable. After the extractive distillation, the solvent may be separated from the recovered mixture of the solvent and HCFC-1233zd(t), for example, by stripping, then optionally purified, and then reintroduced into the extractive distillation tower.

In the invention, the amount of the solvent in the extractive distillation tower is not particularly limited. In the distillation, HFC-245fa can effectively be separated from the crude HFC-245fa by increasing the ratio of the solvent to the fresh-feed in the tower. If this ratio is too high, it may be necessary to provide large devices for the distillation and raise the cost of utilities (e.g., electricity) for conducting the distillation and the like. Thus, this is not preferable from the economical viewpoint. In contrast, if the ratio is too low, the separation efficiency of HFC-245fa may become too low. Thus, the final product may also become too low in purity. In the extractive distillation of the invention, the weight ratio of the solvent to the fresh-feed may be from 10:100 to 2,000:100, preferably from 50:100 to 500:100.

The following nonlimiting examples are illustrative of the present invention.

EXAMPLE 1

In this example, the extractive distillation was conducted, as follows, by using a rectification tower which had a tower diameter of 13 mm and theoretical 12 stages and was made of glass and packed with a stainless steel packing, HELI-PACK (trade name) of Tokyo Tokushu Kana-ami Co. In this distillation, a fresh-feed having a composition shown in Table 1 was introduced into the tower from the stage 10 below the top of the tower at a rate of 31.0 g/hr as shown in Table 1, and 1,1,1,3,3-pentachloropropane (solvent) was introduced into the tower from the stage 4 below the top of the tower at a rate of 98.3 g/hr as shown in Table 1. The distillation was conducted under normal pressure, with a reflux ratio of 4, at a bottom temperature of 50° C. With this, a distillate having a composition shown in Table 1 was withdrawn from the top of the tower at a rate of 12.6 g/hr as shown in Table 1, and the bottom products (liquid) were collected at a rate of 115.2 g/hr as shown in Table 1.

TABLE 1

|  | Fresh-Feed | Solvent | Distillate | Bottom Products |
|---|---|---|---|---|
| Introduction or Formation Rate (g/hr) | 31.0 | 98.3 | 12.6 | 115.2 |
| Composition (wt %) |  |  |  |  |
| HCFC-1233zd(t) | 43.8 | — | 0.7 | 11.1 |
| HCFC-1233zd(c) | 5.1 | — | — | 1.3 |
| HFC-245fa | 51.1 | — | 99.3 | 2.1 |
| 1,1,1,3,3-penta-chloropropane | — | 99.9 | — | 85.4 |

EXAMPLE 2

In this example, Example 1 was slightly modified as follows. The fresh-feed having a composition shown in Table 2 was introduced into the tower at a rate of 30.9 g/hr as shown in Table 2, and the solvent was introduced into the tower at a rate of 100.5 g/hr as shown in Table 2. The distillation was conducted under normal pressure, with a reflux ratio of 2, at a bottom temperature of 60° C. With this, a distillate having a composition shown in Table 2 was withdrawn from the top of the tower at a rate of 23.0 g/hr as shown in Table 2, and the bottom products (liquid) were collected at a rate of 105.5 g/hr as shown in Table 2.

TABLE 2

|  | Fresh-Feed | Solvent | Distillate | Bottom Products |
|---|---|---|---|---|
| Introduction or Formation Rate (g/hr) | 30.9 | 100.5 | 23.0 | 105.5 |
| Composition (wt %) |  |  |  |  |
| HCFC-1233zd(t) | 10.4 | — | 0.8 | 2.5 |
| HCFC-1233zd(c) | 0.2 | — | — | 0.1 |
| HFC-245fa | 89.4 | — | 99.2 | 4.2 |
| 1,1,1,3,3-penta-chloropropane | — | 99.9 | — | 93.2 |

EXAMPLE 3

In this example, Example 1 was slightly modified as follows. The fresh-feed having a composition shown in Table 3 was introduced into the tower at a rate of 18.1 g/hr as shown in Table 3, and 1,1,1-trifluoro-3,3-dichloropropane (solvent) was introduced into the tower at a rate of 72.4 g/hr as shown in Table 3. The distillation was conducted under normal pressure, with a reflux ratio of 4, at a bottom temperature of 60° C. With this, a distillate having a composition shown in Table 3 was withdrawn from the top of the tower at a rate of 10.0 g/hr as shown in Table 3, and the bottom products (liquid) were collected at a rate of 78.4 g/hr as shown in Table 3.

TABLE 3

|  | Fresh-Feed | Solvent | Distillate | Bottom Products |
|---|---|---|---|---|
| Introduction or Formation Rate (g/hr) | 18.1 | 72.4 | 10.0 | 78.4 |
| Composition (wt %) |  |  |  |  |
| HCFC-1233zd(t) | 10.4 | — | 1.5 | 1.8 |
| HCFC-1233zd(c) | 0.2 | — | — | 0.1 |
| HFC-245fa | 89.4 | — | 98.5 | 7.9 |
| 1,1,1,3,3-tri-fluoro-3,3-dichloropropane | — | 99.9 | — | 90.2 |

EXAMPLE 4

In this example, Example 1 was slightly modified as follows. The fresh-feed having a composition shown in Table 4 was introduced into the tower at a rate of 35.1 g/hr as shown in Table 4, and chloroform (solvent) was introduced into the tower at a rate of 118.7 g/hr as shown in Table 4. A distillate having a composition shown in Table 4 was withdrawn from the top of the tower at a rate of 15.9 g/hr as shown in Table 4, and the bottom products (liquid) were collected at a rate of 133.8 g/hr as shown in Table 4.

TABLE 4

|  | Fresh-Feed | Solvent | Distillate | Bottom Products |
|---|---|---|---|---|
| Introduction or Formation Rate (g/hr) | 35.1 | 118.7 | 15.9 | 135.8 |
| Composition (wt %) | | | | |
| HCFC-1233zd(t) | 43.8 | — | 0.3 | 10.8 |
| HCFC-1233zd(c) | 5.1 | — | — | 1.1 |
| HFC-245fa | 51.1 | — | 99.7 | 1.0 |
| Chloroform | — | 99.9 | — | 87.1 |

EXAMPLE 5

In this example, Example 1 was slightly modified as follows. The fresh-feed having a composition shown in Table 5 was introduced into the tower at a rate of 40.4 g/hr as shown in Table 5, and trichloroethylene (solvent) was introduced into the tower at a rate of 114.3 g/hr as shown in Table 5. The distillation was conducted under normal pressure, with a reflux ratio of 4, at a bottom temperature of 60° C. With this, distillate having a composition shown in Table 5 was withdrawn from the top of the tower at a rate of 15.3 g/hr as shown in Table 5, and the bottom products (liquid) were collected at a rate of 138.7 g/hr as shown in Table 5.

TABLE 5

|  | Fresh-Feed | Solvent | Distillate | Bottom Products |
|---|---|---|---|---|
| Introduction or Formation Rate (g/hr) | 40.4 | 114.3 | 15.3 | 138.7 |
| Composition (wt %) | | | | |
| HCFC-1233zd(t) | 46.0 | — | 0.4 | 13.2 |
| HCFC-1233zd(c) | 5.6 | — | — | 1.6 |
| HFC-245fa | 48.4 | — | 99.6 | 3.1 |
| Trichloroethylene | — | 99.9 | — | 82.1 |

EXAMPLE 6

In this example, Example 1 was slightly modified as follows. The fresh-feed having a composition shown in Table 6 was introduced into the tower at a rate of 40.0 g/hr as shown in Table 6, and trichloroethylene (solvent) was introduced into the tower at a rate of 120.0 g/hr as shown in Table 6. The distillation was conducted under normal pressure, with a reflux ratio of 4, at a bottom temperature of 60° C. With this, distillate having a composition shown in Table 6 was withdrawn from the top of the tower at a rate of 30.8 g/hr as shown in Table 6, and the bottom products (liquid) were collected at a rate of 128.2 g/hr as shown in Table 6.

TABLE 6

|  | Fresh-Feed | Solvent | Distillate | Bottom Products |
|---|---|---|---|---|
| Introduction or Formation Rate (g/hr) | 40.0 | 120.0 | 30.8 | 128.2 |
| Composition (wt %) | | | | |
| HCFC-1233zd(t) | 10.4 | — | 0.1 | 3.2 |

TABLE 6-continued

|  | Fresh-Feed | Solvent | Distillate | Bottom Products |
|---|---|---|---|---|
| HCFC-1233zd(c) | 0.2 | — | — | 0.1 |
| HFC-245fa | 89.4 | — | 99.9 | 3.3 |
| Trichloroethylene | — | 99.9 | — | 93.3 |

EXAMPLE 7

In this example, Example 1 was slightly modified as follows. The fresh-feed having a composition shown in Table 7 was introduced into the tower at a rate of 31.5 g/hr as shown in Table 7, and tetrachloroethylene (solvent) was introduced into the tower at a rate of 170.9 g/hr as shown in Table 7. The distillation was conducted under normal pressure, with a reflux ratio of 4, at a bottom temperature of 60° C. With this, distillate having a composition shown in Table 7 was withdrawn from the top of the tower at a rate of 13.6 g/hr as shown in Table 7, and the bottom products (liquid) were collected at a rate of 186.4 g/hr as shown in Table 7.

TABLE 7

|  | Fresh-Feed | Solvent | Distillate | Bottom Products |
|---|---|---|---|---|
| Introduction or Formation Rate (g/hr) | 31.5 | 170.9 | 13.6 | 186.4 |
| Composition (wt %) | | | | |
| HCFC-1233zd(t) | 43.8 | — | 0.2 | 7.2 |
| HCFC-1233zd(c) | 5.1 | — | — | 0.8 |
| HFC-245fa | 51.1 | — | 99.8 | 1.3 |
| Tetrachloroethylene | — | 99.9 | — | 90.7 |

COMPARATIVE EXAMPLE 1

In this comparative example, Example 1 was slightly modified as follows. In fact, the introduction of the solvent was omitted in the distillation, and the fresh-feed having a composition shown in Table 8 was introduced into the tower at a rate of 31.0 g/hr as shown in Table 8. The distillation was conducted under normal pressure, with a reflux ratio of 4, at a bottom temperature of 20° C. With this, distillate having a composition shown in Table 8 was withdrawn from the top of the tower at a rate of 29.6 g/hr as shown in Table 8.

TABLE 8

|  | Fresh-Feed | Solvent | Distillate | Bottom Products |
|---|---|---|---|---|
| Introduction or Formation Rate (g/hr) | 31.0 | — | 29.6 | — |
| Composition (wt %) | | | | |
| HCFC-1233zd(t) | 44.3 | — | 44.8 | — |
| HCFC-1233zd(c) | 8.1 | — | 7.7 | — |
| HFC-245fa | 47.6 | — | 47.4 | — |

EXAMPLE 8

In this example, Example 1 was slightly modified as follows. The fresh-feed having a composition shown in Table 9 was introduced into the tower at a rate of 36.0 g/hr as shown in Table 9, and n-heptane (solvent) was introduced into the tower at a rate of 29.0 g/hr as shown in Table 9. The distillation was conducted under normal pressure, with a reflux ratio of 4, at a bottom temperature of 60° C. With this, distillate having a composition shown in Table 9 was withdrawn from the top of the tower at a rate of 25.4 g/hr as shown in Table 9, and the bottom products (liquid) were collected at a rate of 39.6 g/hr as shown in Table 9.

TABLE 9

|  | Fresh-Feed | Solvent | Distillate | Bottom Products |
|---|---|---|---|---|
| Introduction or Formation Rate (g/hr) | 36.0 | 29.0 | 25.4 | 39.6 |
| Composition (wt %) |  |  |  |  |
| HCFC-1233zd(t) | 14.8 | — | 0.1 | 13.4 |
| HCFC-1233zd(c) | 5.1 | — | 0.0 | 4.6 |
| HFC-245fa | 80.1 | — | 99.9 | 8.7 |
| n-heptane | — | 99.9 | — | 73.3 |

EXAMPLE 9

In this example, Example 1 was slightly modified as follows. The fresh-feed having a composition shown in Table 10 was introduced into the tower at a rate of 45.0 g/hr as shown in Table 10, and methylcyclohexane (solvent) was introduced into the tower at a rate of 32.1 g/hr as shown in Table 10. The distillation was conducted under normal pressure, with a reflux ratio of 2, at a bottom temperature of 60° C. With this, distillate having a composition shown in Table 10 was withdrawn from the top of the tower at a rate of 33.4 g/hr as shown in Table 10, and the bottom products (liquid) were collected at a rate of 43.7 g/hr as shown in Table 10.

TABLE 10

|  | Fresh-Feed | Solvent | Distillate | Bottom Products |
|---|---|---|---|---|
| Introduction or Formation Rate (g/hr) | 45.0 | 32.1 | 33.4 | 43.7 |
| Composition (wt %) |  |  |  |  |
| HCFC-1233zd(t) | 14.8 | — | 0.3 | 15.0 |
| HCFC-1233zd(c) | 5.1 | — | 0.0 | 4.6 |
| HFC-245fa | 80.1 | — | 99.7 | 6.3 |
| Methylcyclohexane | — | 99.9 | — | 73.4 |

EXAMPLE 10

In this example, Example 1 was slightly modified as follows. The fresh-feed having a composition shown in Table 11 was introduced into the tower at a rate of 18.1 g/hr as shown in Table 11, and n-heptane (solvent) was introduced into the tower at a rate of 120.0 g/hr as shown in Table 11. The distillation was conducted under normal pressure, with a reflux ratio of 5, at a bottom temperature of 60° C. With this, distillate having a composition shown in Table 11 was withdrawn from the top of the tower at a rate of 20.8 g/hr as shown in Table 11, and the bottom products (liquid) were collected at a rate of 137.2 g/hr as shown in Table 11.

TABLE 11

|  | Fresh-Feed | Solvent | Distillate | Bottom Products |
|---|---|---|---|---|
| Introduction or Formation Rate (g/hr) | 38.0 | 120.0 | 20.8 | 137.2 |
| Composition (wt %) |  |  |  |  |
| HCFC-1233zd(t) | 35.6 | — | 0.3 | 9.8 |
| HCFC-1233zd(c) | 5.1 | — | — | 1.4 |
| HFC-245fa | 59.3 | — | 99.7 | 1.3 |
| n-heptane | — | 99.9 | — | 87.4 |

COMPARATIVE EXAMPLE 2

In this comparative example, Example 1 was slightly modified as follows. In fact, the introduction of the solvent was omitted in the distillation, and the fresh-feed having a composition shown in Table 12 was introduced into the tower at a rate of 40.0 g/hr as shown in Table 12. The distillation was conducted under normal pressure, with a reflux ratio of 4, at a bottom temperature of 20° C. With this, distillate having a composition shown in Table 12 was withdrawn from the top of the tower at a rate of 39.6 g/hr as shown in Table 12.

TABLE 12

|  | Fresh-Feed | Solvent | Distillate | Bottom Products |
|---|---|---|---|---|
| Introduction or Formation Rate (g/hr) | 40.0 | — | 39.6 | — |
| Composition (wt %) |  |  |  |  |
| HCFC-1233zd(t) | 14.8 | — | 14.9 | — |
| HCFC-1233zd(c) | 5.1 | — | 5.3 | — |
| HFC-245fa | 80.1 | — | 79.8 | — |

What is claimed is:

1. A method for purifying a crude 1,1,1,3,3-pentafluoropropane comprising 1,1,1,3,3-pentafluoropropane and 1-chloro-3,3,3-trifluoro-trans-1-propene, said method comprising distilling the crude 1,1,1,3,3-pentafluoropropane in the presence of a solvent having a boiling point which is higher than that of said 1-chloro-3,3,3-trifluoro-trans-1-propene, thereby substantially removing said 1-chloro-3,3,3-trifluoro-trans-1-propene from said crude 1,1,1,3,3-pentafluoropropane.

2. A method according to claim 1, wherein said solvent is selected from the group consisting of carbon chlorides, chlorohydrocarbons, fluorochlorohydrocarbons, and mixtures thereof.

3. A method according to claim 2, wherein said solvent is selected from the group consisting of:
   first compounds represented by the formula $CF_YCl_{3-Y}CH_2CHF_WCl_{2-W}$ where Y is an integer of from 0 to 3, W is an integer of from 0 to 2, and when Y is 3 W is not 2,
   second compounds represented by the formula $CHF_MCl_{2-M}CH=CF_NCl_{2-N}$ where M is an integer of from 0 to 2, N is an integer of from 0 to 2, and when M is 2 N is not 2,
   third compounds represented by the formula $CHF_PCl_{1-P}CHCF_QCl_{3-Q}$ where P is 0 or 1, and Q is an integer of from 0 to 2, and
   mixtures thereof.

4. A method according to claim 2, wherein said chlorohydrocarbons are 1,1,1,3,3-pentachloropropane, 1,3,3,3-tetrachloropropene, 1,1,3,3-tetrachloropropene and mixtures thereof.

5. A method according to claim 2, wherein said fluorochlorohydrocarbons are 1,1,1-trifluoro-3,3-dichloropropane, 1,1,1,3-tetrafluoro-3-chloropropane, and mixtures thereof.

6. A method according to claim 2, wherein said solvent is selected from the group consisting of a chlorine-containing ethane having a chlorine atom number of from 3 to 5, a chlorine-containing ethylene having a chlorine atom number of from 3 to 4, a chlorine-containing methane having a chlorine atom number of from 2 to 3, and mixtures thereof.

7. A method according to claim 2, wherein said solvent is selected from the group consisting of trichloroethylene, tetrachloroethylene, 1,1,2-trichloroethane, 1,1,2,2-tetrachloroethane, 1,1,1,2-tetrachloroethane, pentachloroethane, dichloromethane, chloroform, and mixtures thereof.

8. A method according to claim 1, wherein a molar ratio of said 1-chloro-3,3,3-trifluoro-trans-1-propene to said 1,1,1,3,3-pentafluoropropane is from 0.01:1 to 1:1.

9. A method according to claim 1, wherein a weight ratio of said solvent to said crude 1,1,1,3,3-pentafluoropropane is from 10:100 to 2,000:100.

10. A method according to claim 9, wherein said weight ratio is from 50:100 to 500:100.

11. A method according to claim 1, wherein said solvent is at least one compound selected from saturated hydrocarbons.

12. A method according to claim 11, wherein said saturated hydrocarbon has a carbon atom number of from 5 to 10, a melting point of not higher than −10° C., and a boiling point of from 35 to 200° C.

13. A method according to claim 12, wherein said saturated hydrocarbon is one of an acyclic saturated hydrocarbon which is optionally formed with a branch and a cyclic saturated hydrocarbon which is optionally formed with a substituent group.

14. A method according to claim 11, wherein said saturated hydrocarbon is one of n-heptane and methylcyclohexane.

15. A method for purifying a crude 1,1,1,3,3-pentafluoropropane comprising 1,1,1,3,3-pentafluoropropane and 1-chloro-3,3,3-trifluoro-trans-1-propene, said method comprising extractive distilling said crude 1,1,1,3,3-pentafluoropropane in the presence of a solvent having a boiling point which is higher than that of said 1-chloro-3,3,3-trifluoro-trans 1-propene, thereby substantially removing said 1-chloro-3,3,3 trifluoro-trans-1-propene from said crude 1,1,1,3,3 pentafluoropropane.

16. A method according to claim 15, wherein said solvent is an extracting reagent selected from the group consisting of carbon chlorides, chlorohydrocarbons, fluorochlorohydrocarbons, and mixtures thereof.

17. A method according to claim 15, wherein said solvent is an extracting reagent which is at least one compound selected from saturated hydrocarbons.

* * * * *